US010502701B2

(12) United States Patent
Lobastov et al.

(10) Patent No.: US 10,502,701 B2
(45) Date of Patent: Dec. 10, 2019

(54) METHOD AND SYSTEM USING X-RAY PINHOLE CAMERA FOR IN-SITU MONITORING OF ELECTRON BEAM MANUFACTURING PROCESS

(71) Applicant: General Electric Company, Schenectady, NY (US)

(72) Inventors: Vladimir Anatolievich Lobastov, Waterford, NY (US); Adrian Ivan, Niskayuna, NY (US); David Charles Bogdan, Jr., Charlton, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/941,245

(22) Filed: Mar. 30, 2018

(65) Prior Publication Data
US 2019/0302043 A1    Oct. 3, 2019

(51) Int. Cl.
*B33Y 30/00* (2015.01)
*B23K 15/02* (2006.01)
(Continued)

(52) U.S. Cl.
CPC ..... *G01N 23/2252* (2013.01); *B23K 15/0086* (2013.01); *B23K 15/02* (2013.01);
(Continued)

(58) Field of Classification Search
CPC ............... B22F 3/1055; B22F 2202/11; B22F 2203/00; B33Y 10/00; B33Y 50/02; B33Y 50/00; Y02P 10/24; H01J 2237/2445; H01J 2237/30472; H01J 37/244; H01J 37/30; H01J 37/3005; H01J 37/304; G01N 23/2252; G01N 2223/629; G01N 23/04; G01N 23/046; G01N 23/22; G01N 23/2251; G05B 2219/35134
(Continued)

(56) References Cited

U.S. PATENT DOCUMENTS 4,843,246 A    6/1989    Benes et al.
6,652,143 B2   11/2003   Popescu
(Continued)

FOREIGN PATENT DOCUMENTS

WO    2017087451 A1    5/2017

OTHER PUBLICATIONS

Gong et al.,"Review on Powder-Based Electron Beam Additive Manufacturing Technology", The American Society of Mechanical Engineers, pp. 507-515, 2012.

*Primary Examiner* — David A Vanore
(74) *Attorney, Agent, or Firm* — Armstrong Teasdale LLP (57) ABSTRACT

An additive manufacturing system includes a cabinet, an electron beam system, at least one imaging device, and a computing device. The cabinet is configured to enclose a component and defines a pinhole extending therethrough. The electron beam system is configured to generate an electron beam directed toward the component. Interactions between the component and the electron beam generate x-ray radiation. The at least one imaging device is configured to detect the x-ray radiation through the pinhole. The computing device is configured to image the component based on the x-ray radiation detected by the at least one imaging device.

19 Claims, 8 Drawing Sheets

(51) Int. Cl.
*G01N 23/2252* (2018.01)
*B33Y 50/02* (2015.01)
*B23K 15/00* (2006.01)
*B33Y 10/00* (2015.01)

(52) U.S. Cl.
CPC ............... *B33Y 10/00* (2014.12); *B33Y 30/00* (2014.12); *B33Y 50/02* (2014.12); *G01N 2223/646* (2013.01); *G01N 2223/648* (2013.01)

(58) Field of Classification Search
USPC ............... 250/492.1, 492.2, 370.11; 378/193
See application file for complete search history.

(56) References Cited

U.S. PATENT DOCUMENTS

| | | | |
|---|---|---|---|
| 8,570,534 B1 * | 10/2013 | Loewgren | G01B 11/14 356/614 |
| 9,341,467 B2 | 5/2016 | Snis | |
| 9,347,770 B2 | 5/2016 | Snis | |
| 9,406,483 B1 | 8/2016 | Lock | |
| 9,981,341 B2 * | 5/2018 | Mazumder | B23K 26/032 |
| 10,253,618 B2 * | 4/2019 | Safinya | E21B 47/0905 |
| 2002/0079458 A1 * | 6/2002 | Zur | G01T 1/2018 250/370.11 |
| 2005/0053197 A1 * | 3/2005 | Radley | G01N 23/12 378/193 |
| 2015/0037601 A1 * | 2/2015 | Blackmore | B23K 15/002 428/600 |
| 2015/0321422 A1 * | 11/2015 | Boyer | B22F 3/1055 264/497 |
| 2016/0211116 A1 * | 7/2016 | Lock | H01J 37/305 |
| 2017/0001379 A1 * | 1/2017 | Long | B33Y 50/02 |
| 2017/0023499 A1 * | 1/2017 | Mitchell | B33Y 30/00 |
| 2017/0066051 A1 * | 3/2017 | Ackelid | B33Y 10/00 |
| 2017/0087661 A1 * | 3/2017 | Backlund | B33Y 50/00 |
| 2017/0120376 A1 * | 5/2017 | Cheverton | B33Y 50/02 |
| 2017/0136541 A1 * | 5/2017 | Fager | B33Y 10/00 |
| 2018/0095450 A1 * | 4/2018 | Lappas | B33Y 10/00 |
| 2018/0126670 A1 * | 5/2018 | DehghanNiri | B29C 64/386 |
| 2018/0147655 A1 * | 5/2018 | Ackelid | B33Y 10/00 |
| 2018/0154443 A1 * | 6/2018 | Milshtein | B23K 15/0086 |
| 2018/0154484 A1 * | 6/2018 | Hall | B22F 3/1055 |
| 2018/0156745 A1 * | 6/2018 | Hegeman | G01N 23/223 |
| 2018/0186082 A1 * | 7/2018 | Randhawa | B29C 64/135 |
| 2018/0193947 A1 * | 7/2018 | Harding | B23K 26/032 |
| 2018/0236603 A1 * | 8/2018 | Carter | B23K 26/142 |
| 2018/0290381 A1 * | 10/2018 | Volkov | B23K 26/342 |
| 2018/0292331 A1 * | 10/2018 | Gold | B33Y 50/02 |
| 2018/0297115 A1 * | 10/2018 | Diwinsky | B22F 3/1055 |
| 2019/0039134 A1 * | 2/2019 | Vogel | B33Y 40/00 |

* cited by examiner

METHOD AND SYSTEM USING X-RAY PINHOLE CAMERA FOR IN-SITU MONITORING OF ELECTRON BEAM MANUFACTURING PROCESS

BACKGROUND

The field of the disclosure relates to additive manufacturing systems and, more specifically, to x-ray imaging devices for use with Electron Beam Melting (EBM) manufacturing systems and methods of in-situ monitoring and inspecting components manufactured with EBM manufacturing systems.

Additive manufacturing systems and processes are used to fabricate precision three-dimensional components from a digital model. Such components are fabricated using an additive process, where successive layers of material are solidified one on top of the other. At least some known additive manufacturing systems use an energy source and a series of lenses and mirrors to direct a focused energy beam over a powdered material in a pattern provided by a digital material. Some known additive manufacturing systems include Electron Beam Melting (EBM), Direct Metal Laser Melting (DMLM), Selective Laser Sintering (SLS), Direct Metal Laser Sintering (DMLS), Selective Laser Melting (SLM) and Laser Cusing systems.

In some known additive manufacturing systems, layer and component quality is reduced due to variation in heat being transferred to the metal powder by the focused energy beam within the melt pool. For example, sometimes undesirable features such as air pockets, internal voids, and cracking occur within or between build layers. In addition, in some known additive manufacturing systems, heat variation also induces porosity within the build layers. Moreover, variation in energy beam position is also known to generate these undesirable features within the additively manufactured component.

At least some known additive manufacturing systems include imaging devices that generate images of portions of the melt pool during the fabrication process. The imaging devices typically include a static camera with low exposure that tracks the focused energy beam to capture light during the melting process. However, such imaging devices only generate images of visible portions of the component and thus do not capture subsurface features. Other known component inspection techniques include ultrasound and x-ray imaging. However, ultrasound imaging requires that the component be finished, thus further expending time and materials costs for a potentially undesirable part. Additionally, x-ray imaging is typically performed by digital x-ray or Computed Tomography (CT) scans, which are limited by the size of the component and also require a separate x-ray source to generate a large amount of x-ray energy to penetrate the entire component.

BRIEF DESCRIPTION

In one aspect, an additive manufacturing system is provided. The additive manufacturing system includes a cabinet, an electron beam system, at least one imaging device, and a computing device. The cabinet is configured to enclose the component and defines a pinhole extending therethrough, allowing x-rays to escape only through it and, upon incidence on the imaging device, to form an x-ray image according to geometric optics principles. The electron beam system is configured to generate an electron beam directed toward a component. Interactions between the component and the electron beam generate x-ray radiation. The at least one imaging device is configured to detect the x-ray radiation through the pinhole. The computing device is configured to image the component based on the x-ray radiation detected by the at least one imaging device.

In another aspect, an additive manufacturing system is provided. The additive manufacturing system includes a cabinet, an electron beam system, and at least one imaging device. The cabinet is configured to enclose a component. The cabinet includes a top side having a top surface. The top side defines at least one pinhole extending therethrough and an electron beam hole extending therethrough. The electron beam system is configured to generate an electron beam directed through the electron beam hole toward the component. The electron beam system is positioned above the top side of the cabinet. Interactions between the component and the electron beam generate x-ray radiation through processes such as Bremsstrahlung (braking radiation) and x-ray fluorescence. The at least one imaging device is configured to detect the x-ray radiation. The at least one imaging device is positioned above the top surface and outside the cabinet. The x-ray radiation is directed through the at least one pinhole toward the at least one imaging device.

In yet another aspect, a method of monitoring a component manufactured in an additive manufacturing system is provided. The method includes directing an electron beam towards a build layer of the component positioned within a powder bed of the additive manufacturing system. The method also includes detecting by at least one detector the x-ray radiation generated by interactions between the component and the electron beam.

In yet another aspect, a method of calibration of additive manufacturing system is provided. The method includes directing an electron beam with predefined parameters towards a build layer of the component positioned within a powder bed of the additive manufacturing system. The method also includes detecting by at least one detector the x-ray radiation generated by interactions between the component and the electron beam. The method also includes processing and quantifying beam spot size (dimension and coordinates) for at least one electron beam. The method also include provision to generate calibration table for electron beam control parameters and corresponding spot sizes and beam positions on the build plane.

In yet another aspect, a method of in-situ calibration of the position, intensity, size, and/or shape of an electron beam on a powder bed. The method includes directing, using an electron beam system, the electron beam towards a build layer of a component. The electron beam system having a plurality of electron beam parameters including a beam current, a beam voltage, a deflection current, a stigmation current, and a focusing current that at least partially determine the position, the intensity, the size, and the shape of the electron beam. Method also includes detecting by at least one detector the x-ray radiation generated by interactions between the component and the electron beam. Method further includes generating, based on the detected x-ray radiation, an electron beam parameter map. Method also includes determining at least one of the position, the intensity, the size, and the shape of the electron beam using the electron beam map.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately", and "substantially", are not to be limited to the precise value specified. In at least some instances, the approximating language may correspond to the precision of an instrument for measuring the value. Here and throughout the specification and claims, range limitations may be combined or interchanged. Such ranges are identified and include all the sub-ranges contained therein unless context or language indicates otherwise.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random access memory (RAM), a computer-readable non-volatile medium, such as a flash memory. Alternatively, a floppy disk, a compact disc-read only memory (CD-ROM), a magneto-optical disk (MOD), or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Additive manufacturing processes and systems include, for example, and without limitation, vat photopolymerization, powder bed fusion, binder jetting, material jetting, sheet lamination, material extrusion, directed energy deposition and hybrid systems. These processes and systems include, for example, and without limitation, SLA—Stereolithography Apparatus, DLP—Digital Light Processing, 3SP—Scan, Spin, and Selectively Photocure, CLIP—Continuous Liquid Interface Production, SLS—Selective Laser Sintering, DMLS—Direct Metal Laser Sintering, SLM—Selective Laser Melting, EBM—Electron Beam Melting, SHS—Selective Heat Sintering, MJF—Multi-Jet Fusion, 3D Printing, Voxeljet, Polyjet, SCP—Smooth Curvatures Printing, MJM—Multi-Jet Modeling Projet, LOM—Laminated Object Manufacture, SDL—Selective Deposition Lamination, UAM—Ultrasonic Additive Manufacturing, FFF—Fused Filament Fabrication, FDM—Fused Deposition Modeling, LMD—Laser Metal Deposition, LENS—Laser Engineered Net Shaping, DMD—Direct Metal Deposition, Hybrid Systems, and combinations of these processes and systems. These processes and systems may employ, for example, and without limitation, all forms of electromagnetic radiation, heating, sintering, melting, curing, binding, consolidating, pressing, embedding, and combinations thereof.

Additive manufacturing processes and systems employ materials including, for example, and without limitation, polymers, plastics, metals, ceramics, sand, glass, waxes, fibers, biological matter, composites, and hybrids of these materials. These materials may be used in these processes and systems in a variety of forms as appropriate for a given material and the process or system, including, for example, and without limitation, as liquids, solids, powders, sheets, foils, tapes, filaments, pellets, liquids, slurries, wires, atomized, pastes, and combinations of these forms.

Embodiments of imaging systems for additive manufacturing systems, as described herein, overcome a number of deficiencies of known imaging systems and provide a cost-effective method for identifying undesirable features during the additive manufacturing process. Specifically, the embodiments described herein replace known imaging systems that image only a surface of a component build layer. This leads to undesirable subsurface features not being detected until after the additive manufacturing process is completed. More specifically, an exemplary imaging device described herein detects x-rays generated during Electron Beam Additive Manufacturing (EBM). During EBM, an electron beam pre-heats a material, fuses the material, and anneals the material into a shape of a near-final shape metal part. High energy electrons strongly interact with the material during the process and produce x-ray radiation which originates in the volume of the material through processes such as Bremsstrahlung (braking radiation) and x-ray fluorescence. The generated x-rays provide a unique opportunity to monitor the quality of the build process without expensive additional hardware that generates x-rays. The exemplary imaging device described herein includes an x-ray detector that images the component by detecting x-rays generated during the additive manufacturing process. The x-rays reveal undesirable subsurface features not normally detectable by surface-only imaging devices. Through use of x-rays, undesirable subsurface features such as voids, cracks, and porosity are identified. By identifying these subsurface features early in the additive manufacturing process, the manufacturing process can be adjusted to fix the features and allow for early detection of an unusable component, thereby increasing manufacturing efficiencies.

Additionally, embodiments of x-ray imaging systems for use with an additive manufacturing component, as described herein, overcome a number of deficiencies of known imaging systems and provide a cost-effective method for identifying undesirable features during the additive manufacturing process. Specifically, the embodiments described herein replace known 'ex situ' imaging systems such as computed tomography scan systems and digital x-ray systems that are limited as to the size of the component that may fit within the scanning system after its manufacturing. Additionally, the embodiments described herein replace ultrasound imaging systems that require the component surface to be finished. These known systems lead to undesirable subsurface features not being detected for large components or not being detected until after the component is manufactured. More specifically, the exemplary imaging systems described herein include an x-ray device that images a localized predetermined area of the component through use of x-rays. In some embodiments, these images are combined to form a complete representation of the component. Through use of the x-ray system, undesirable subsurface features such as voids, cracks, and porosity are identified for large additive manufactured components. As such, the size of the component does not determine what imaging technique to use as the imaging system size is not a factor. Moreover, the surface of component does not need to be finished before imaging, thereby decreasing manufacturing costs for undesirable components.

Figure 1:
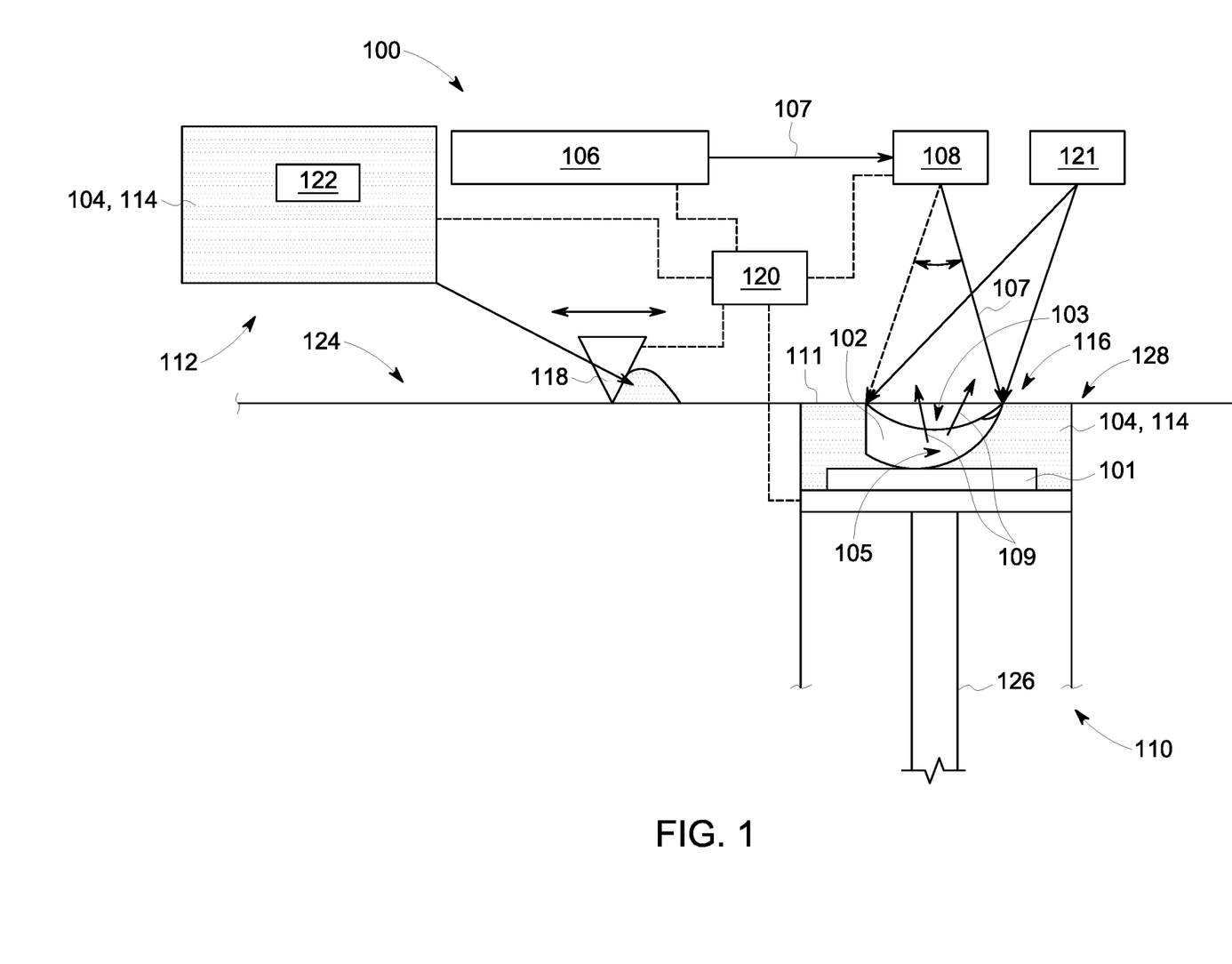
FIG. 1 is a block diagram of an exemplary additive manufacturing system.

FIG. 1 is a block diagram of an exemplary embodiment of an additive manufacturing system 100. In the exemplary embodiment, additive manufacturing system 100 is an EBM system. In alternative embodiments, additive manufacturing system 100 is any other suitable additive manufacturing system, including, without limitation, one of a Direct Metal Laser Sintering (DMLS) system, a Direct Metal Laser Melting (DMLM) system, a Selective Laser Sintering (SLS) system, a Direct Metal Laser Deposition (DMLD) system, a Direct Metal Laser Deposition (DMLD) system, and a LaserCusing® system. In the exemplary embodiment, additive manufacturing system 100 includes a build fixture 110, a build plate 101 oriented within build fixture 110 and configured to support component 102, an electron beam system 106 configured to generate an electron beam 107, optionally, a scanner system 108 configured to selectively direct electron beam 107 across build fixture 110 at a preselected scan speed, a powder delivery system 112, a powder coater 118, a controller 120, and an imaging device 121.

In the exemplary embodiment, powder coater 118 is movable, upon instruction by controller 120, to transfer material 104 in powdered form 114 from powder delivery system 112 to a powder bed 111 within build fixture 110. For example, in the exemplary embodiment, powder delivery system 112 includes a hopper 122 operable, upon instruction by controller 120, to release a predetermined amount of material 104 in powdered form 114 to a staging area 124 of powder delivery system 112, and powder coater 118 is sweepable along area 124 to capture material 104 in powdered form 114 and deliver it to build fixture 110. Powder coater 118 is further operable to deposit the captured material 104 in powdered form 114 atop build fixture 110 as a build layer 116. Moreover, build fixture 110 is operable, upon instruction by controller 120, to reposition build plate 101 to receive build layer 116 atop previously deposited layers of material 104. For example, in the exemplary embodiment, build fixture 110 includes a piston 126 operable, upon instruction by controller 120, to lower build plate 101 a preselected distance below an edge 128 of build fixture 110 to accommodate receipt of build layer 116 from powder coater 118. In alternative embodiments, additive manufacturing system 100 is configured to deposit material 104 in powdered form 114 onto build layer 116 in any manner that enables component 102 to be formed as described herein.

In the exemplary embodiment, electron beam system 106 is configured, upon instruction by controller 120, to generate electron beam 107 having a preselected energy sufficient to at least partially melt material 104 in powdered form 114 at preselected regions of build layer 116, such that the preselected regions fuse with material 104 in a layer immediately below build layer 116. In the exemplary embodiment, electron beam system 106 includes an electron beam gun configured to generate electron beam 107. The preselected energy of electron beam 107 is determined by a beam current and a beam voltage delivered to electron beam system 106. Varying the beam current or beam voltage varies the energy of electron beam 107. In alternative embodiments, electron beam system 106 includes any suitable source for electron beam 107 that enables component 102 to be formed as described herein. Additionally, although additive manufacturing system 100 is described as including a single electron beam system 106, it should be understood that additive manufacturing system 100 may include more than one electron beam system 106. In some embodiments, for example, additive manufacturing system 100 includes a first electron beam system 106 having a first power and a second electron beam system 106 having a second power different from the first power. In other embodiments, additive manufacturing system 100 includes any combination of electron beam systems 106 each having any suitable power that enables component 102 to be formed as described herein.

In the exemplary embodiment, scanner system 108 is configured, upon instruction by controller 120, to selectively direct electron beam 107 to preselected regions of build layer 116 that correspond to portions of component 102, such that the preselected regions fuse with material 104 in a layer immediately below build layer 116. For example, scanner system 108 may include a scanning coil system including a plurality of electromagnetic coils configured to selectively direct electron beam 107 to preselected regions of build layer 116. In the exemplary embodiment, the scanning coil system 108 selectively directs electron beam 107 to preselected regions of build layer 116 by creating a magnetic field which magnetically directs electron beam 107. The magnetic field is generated by passing at least one current through a plurality of coils (not shown) within scanner system 108. The coils may include a plurality of coils (each configured to generate a plurality of different currents and magnetic fields) each configured to change a different parameter of electron beam 107. Varying the current through the coils changes various parameters of electron beam 107. For example, the coils may include deflection coils, stigmation coils, and focusing coils. Varying a deflection current through the deflection coils varies a position of electron beam 107. Similarly, varying a stigmation current through the stigmation coils and varying a focusing current through the focusing coils varies a size and a shape of electron beam 107. In alternative embodiments, scanner system 108 include any device configured to selectively direct electron beam 107 to preselected regions of build layer 116. Scanner system 108 may also include systems for determining a position and orientation of build layer 116 with respect to electron beam 107. For example, scanner system 108 may also include a suitable sensor, such as at least one of a two-dimension (2D) scan galvanometer, a three-dimension (3D) scan galvanometer, and a dynamic focusing scan galvanometer (not shown), to determine a position and orientation of build layer 116 with respect to electron beam 107. In alternative embodiments, scanner system 108 is configured to selectively direct electron beam 107 to the preselected regions of build layer 116 in any suitable fashion that enables additive manufacturing system 100 to function as described herein.

Controller 120 is operably coupled to each of build fixture 110, electron beam system 106, scanner system 108, powder delivery system 112, powder coater 118, and imaging device 121 to implement additive manufacturing system 100 as a computer numerically controlled (CNC) machine. In the exemplary embodiment, to form component 102, controller 120 receives a computer design model of component 102 and generates a build file in which the computer design model is "sliced" into a series of thin, parallel planes, such that a distribution of material 104 within each plane is defined. Controller 120 then provides command signals to, and receives feedback from, build fixture 110, electron beam system 106, scanner system 108, powder delivery system 112, and powder coater 118 as necessary to deposit and fuse successive layers of material 104 in accordance with the model slices to form component 102. For example, controller 120 is configured to control build fixture 110, powder delivery system 112, and powder coater 118 to provide material 104 in powdered form 114 for each successive build layer 116, and to control the power output of electron beam system 106 and the position, movement, and scan speed of scanner system 108, such that electron beam 107 follows a predetermined path along each build layer 116, such that material 104 is selectively fused to form each layer of component 102 having a fused layer thickness in accordance with the build file.

In the exemplary embodiment, component 102 as formed includes an exterior surface 103 and an interior volume of material 105. In the exemplary embodiment, electron beam 107 generates high energy electrons which interact with volume of material 105 during the manufacturing process and produce x-ray radiation 109 originating in interior volume of material 105. Imaging device 121 is configured to detect x-ray radiation 109. In the exemplary embodiment, imaging device 121 includes at least one digital x-ray panel configured to detect x-ray radiation 109. In alternative embodiments, imaging device 121 includes any suitable device that detects x-rays as described herein. Additionally, imaging device 121 may include more than one digital x-ray panel configured to detect x-ray radiation 109. In alternative embodiments, imaging device 121 may include a plurality of digital x-ray panels configured to detect x-ray radiation 109.

In the exemplary embodiment, controller 120 is implemented using one or more electronic computing devices. Such devices typically include at least one processing device (not shown) such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, or any other circuit or processing device capable of executing the functions described herein. The methods described herein may be encoded as executable instructions embodied in a computer readable medium, including, without limitation, a non-transitory storage device or a memory device coupled to the at least one processor. Such instructions, when executed by the controller or processing device, cause the controller or processing device to perform at least some of the method steps described herein. Although controller 120 is illustrated as a discrete system, controller 120 may be implemented at least partially by at least one processor embedded within any of build fixture 110, electron beam system 106, scanner system 108, powder delivery system 112, and powder coater 118, and any other suitable computing devices. The above examples are exemplary only, and thus are not intended to limit in any way the definition or meaning of the terms controller and processing device.

For example, in certain embodiments, controller 120 is configured to operate at least one electron beam system 106 and scanner system 108 using preselected operating parameters that result in the creation of component 102. For example, in one embodiment, the preselected operating parameters may include a power of electron beam 107 generated by electron beam system 106 in a range from about 100 watts to about 6,000 watts, and a scan speed of scanner system 108 in a range of from about 50 millimeters per second to about 25,000 millimeters per second, such that a thickness of each fused build layer 116 of component 102 is in a range from about 10 micrometers to about 200 micrometers.

In operation, additive manufacturing system 100 fabricates component 102 by a layer-by-layer manufacturing process. More specifically, component 102 is fabricated from an electronic representation of the three-dimensional geometry of component 102 stored on controller 120. For example, the electronic representation is produced in a computer aided design (CAD) or similar electronic file. In alternative embodiments, the electronic representation is any electronic representation that enables additive manufacturing system 100 to operate as described herein. In the exemplary embodiment, the CAD file representing component 102 is converted, for example, by controller 120, into a layer-by-layer format that includes a plurality of build parameters of each layer. Component 102 is arranged electronically in a desired orientation relative to the origin of the coordinate system used in additive manufacturing system 100. Additionally, the geometry of component 102 is sliced into a stack of two-dimensional layers of a desired thickness, such that the geometry of each layer is an outline of the cross-section through component 102 at that particular layer location. A hatch pattern is generated within each respective layer such that the build parameters are applied along the hatch pattern to fabricate that layer of component 102 from build powdered material 114 and constructing a plan to build component 102. The steps are repeated for each respective layer. Once the process is completed, an electronic computer build file (or files) is generated including all of the layers. During or after each build layer 116, imaging device 121 and controller 120 are used to record and store data images of the recent build layer 116 that are then compared to the electronic computer build files to verify the manufacturing process. Imaging device 121 is discussed in further detail below in reference to FIGS. 2-8.

After the build file is generated, additive manufacturing system 100 is operated to manufacture component 102 by implementing the layer-by-layer manufacturing process plan that is constructed. The exemplary layer-by-layer manufacturing process does not use a pre-existing article as the precursor to the final component, rather the process produces component 102 from a raw material in a configurable form, such as the powdered material 114. For example, and without limitation, a steel alloy material is additively manufactured using a steel alloy powder. Additive manufacturing system 100 enables fabrication of components using a broad range of materials, for example, metals, ceramics, and polymers.

Controller 120 includes at least one memory device and at least one processor coupled to the memory device. In some embodiments, the processor includes one or more processing units, such as, without limitation, a multi-core configuration. In the exemplary embodiment, the processor includes a field programmable gate array (FPGA). Alternatively, the processor is any type of processor that permits controller 120 to operate as described herein. In some embodiments, executable instructions are stored in the memory device. Controller 120 is configurable to perform one or more operations described herein by the programming processor. For example, the processor is programmed by encoding an operation as one or more executable instructions and providing the executable instructions in the memory device. In the exemplary embodiment, the memory device is one or more devices that enable storage and retrieval of information such as executable instructions or other data. In some embodiments, the memory device includes one or more computer readable media, such as, without limitation, random access memory (RAM), dynamic RAM, static RAM, a solid-state disk, a hard disk, read-only memory (ROM), erasable programmable ROM, electrically erasable programmable ROM, or non-volatile RAM memory. The above memory types are exemplary only, and are thus not limiting as to the types of memory usable for storage of a computer program.

In the exemplary embodiment, the memory device is configured to store build parameters including, without limitation, real-time and historical build parameter values, or any other type of data. In the exemplary embodiment, the memory device stores images generated by imaging device 121. In alternative embodiments, the memory device stores any data that enable additive manufacturing system 100 to operate as described herein. In some embodiments, the processor removes or "purges" data from the memory device based on the age of the data. For example, the processor overwrites previously recorded and stored data associated with a subsequent time or event. In addition, or alternatively, the processor removes data that exceeds a predetermined time interval. In addition, the memory device includes, without limitation, sufficient data, algorithms, and commands to facilitate monitoring and measuring of build parameters and the geometric conditions of component 102 fabricated by additive manufacturing system 100.

Optionally, controller 120 may also include a presentation interface coupled to the processor. Presentation interface presents information, such as images generated by imaging device 121, to a user. In one embodiment, presentation interface includes a display adapter (not shown) coupled to a display device (not shown), such as a cathode ray tube (CRT), a liquid crystal display (LCD), an organic LED (OLED) display, or an "electronic ink" display. In some embodiments, presentation interface includes one or more display devices. In addition, or alternatively, presentation interface includes an audio output device (not shown), for example, without limitation, an audio adapter or a speaker (not shown).

Optionally, controller 120 may also include a user input interface. In the exemplary embodiment, the user input interface is coupled to the processor and receives input from the user. In some embodiments, user input interface includes, for example, without limitation, a keyboard, a pointing device, a mouse, a stylus, a touch sensitive panel, such as, without limitation, a touch pad or a touch screen, or an audio input interface, such as, without limitation, a microphone. In further embodiments, a single component, such as a touch screen, functions as both a display device of the presentation interface and the user input interface.

Optionally, a communication interface may be coupled to the processor and is configured to be coupled in communication with one or more other devices to perform input and output operations with respect to such devices while performing as an input channel. For example, in some embodiments, the communication interface includes, without limitation, a wired network adapter, a wireless network adapter, a mobile telecommunications adapter, a serial communication adapter, or a parallel communication adapter. Communication interface receives a data signal from or transmits a data signal to one or more remote devices.

The presentation interface and the communication interface are both capable of providing information suitable for use with the methods described herein, such as, providing information to the user or processor. Accordingly, the presentation interface and the communication interface are referred to as output devices. Similarly, the user input interface and the communication interface are capable of receiving information suitable for use with the methods described herein and are referred to as input devices.

Figure 2:
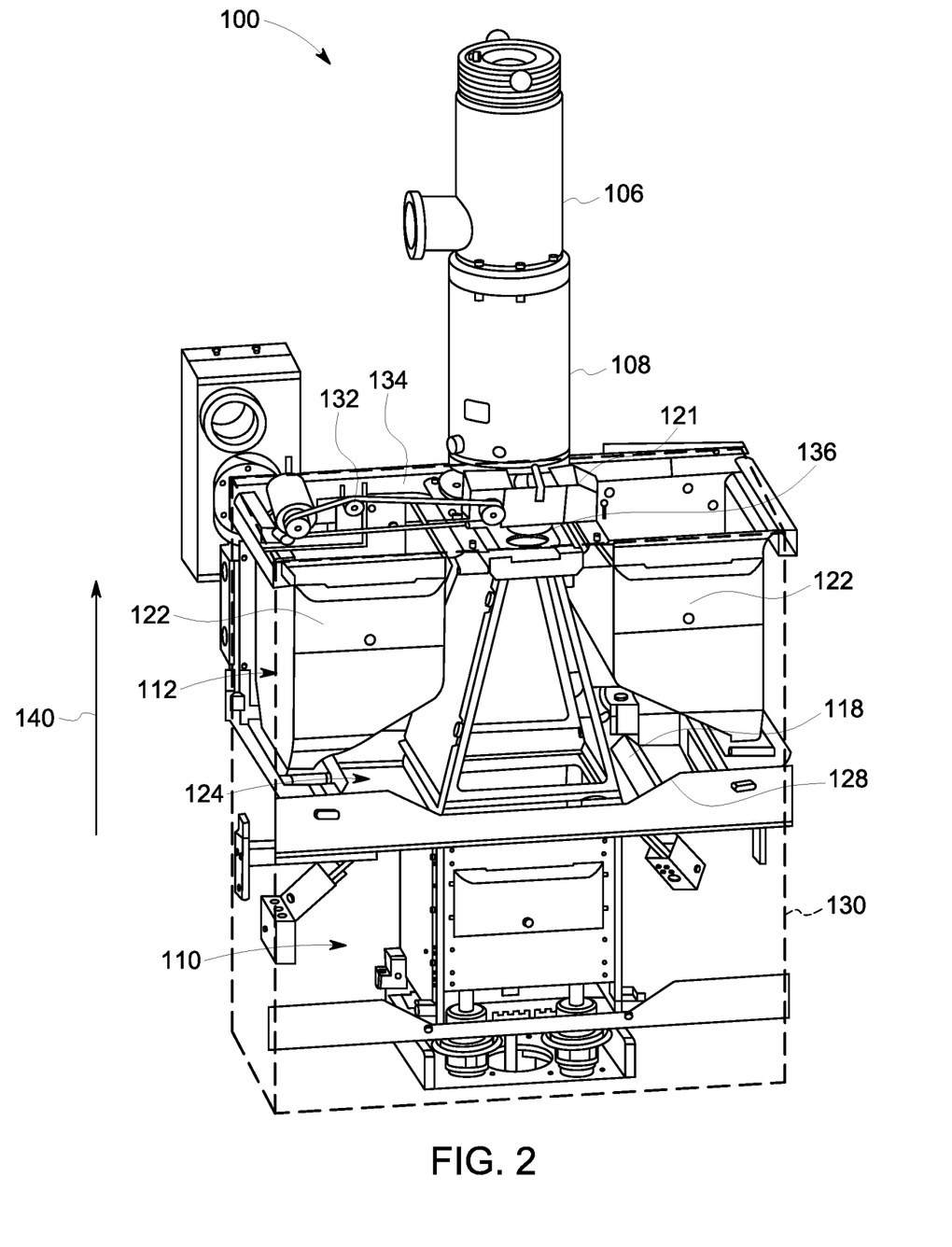
FIG. 2 is a schematic perspective view of the additive manufacturing system shown in FIG. 1.
Figure 3:
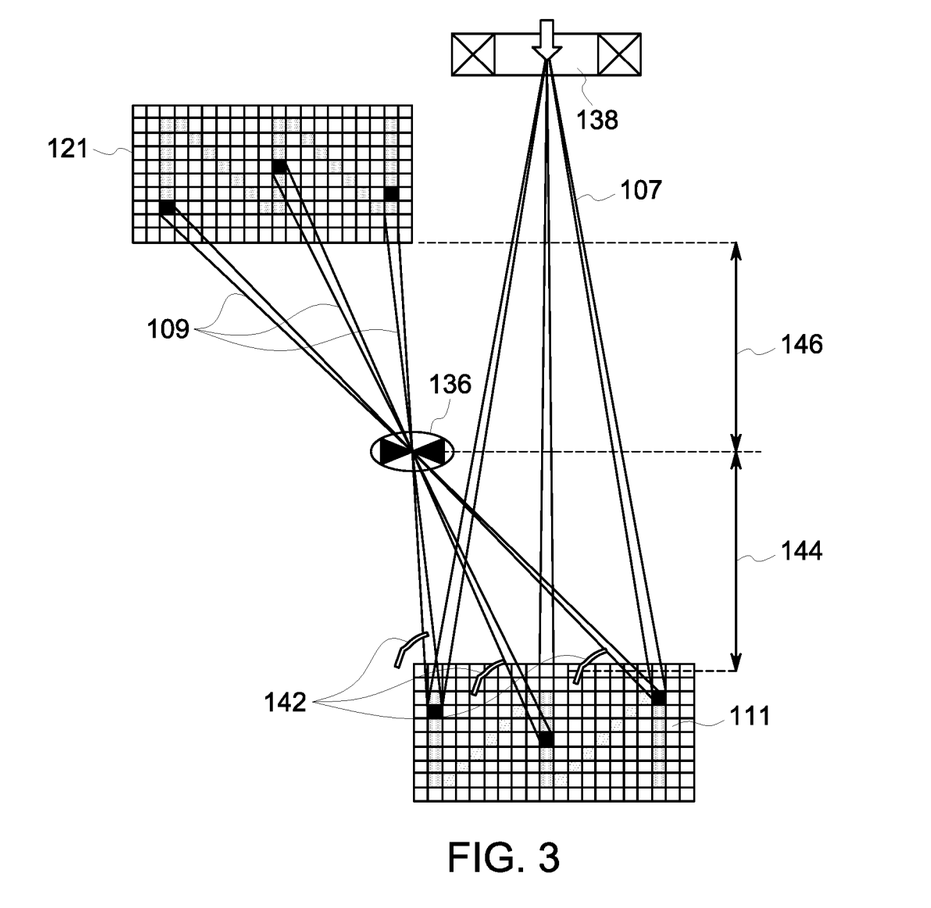
FIG. 3 is a block diagram of the arrangement of an imaging device, a component, and a pinhole relative to each other in the additive manufacturing system shown in FIG. 1.

FIG. 2 is a schematic perspective view of additive manufacturing system 100. FIG. 3 is a block diagram of the arrangement of imaging device 121, powder bed 111, and a pinhole 136 relative to each other in additive manufacturing system 100. As shown in FIG. 2 and FIG. 3, additive manufacturing system 100 is positioned within a cabinet 130 configured to contain build fixture 110, powder delivery system 112, and powder coater 118. Electron beam system 106, scanner system 108, and imaging device 121 are positioned on top of cabinet 130. In the exemplary embodiment, cabinet 130 includes a top side 132 having a top surface 134. Top side 132 defines at least one pinhole 136 extending therethrough and an electron beam port 138 extending therethrough. Imaging device 121 is configured to detect x-rays through pinhole 136 and electron beam system 106 is configured to direct electron beam 107 through electron beam port 138. As used herein, the term "pinhole" refers to a conduit that directs x-rays generated from a generation source to a detector. In the exemplary embodiment, pinhole 136 is a conduit through cabinet 130 that directs x-ray radiation 109 to imaging device 121. In the exemplary embodiment, pinholes 136 are circular or oval shaped conduits extending through cabinet 130. In alternative embodiments, pinholes 136 may have any shape and dimension that enables additive manufacturing system 100 to operate as described herein.

Imaging device 121 includes at least one digital x-ray panel coupled to controller 120 and positioned above build fixture 110 in a vertical direction 140. In the exemplary embodiment, imaging device 121 is positioned at a stationary location above cabinet 130. Components of imaging device 121 are positioned at angles 142 (shown in FIG. 3) in relation to build layer 116, such that x-ray radiation 109 is received and detected from component 102. In alternative embodiments, imaging device 121 includes at least one digital x-ray panel positionable, by controller 120, within additive manufacturing system 100. That is, in such embodiments, imaging device 121 is not stationary, but rather can be positioned around additive manufacturing system 100 to image component 102.

In another embodiment, imaging device 121 includes a plurality of digital x-ray panels positioned at stationary locations above cabinet 130. Each digital x-ray panel is positioned at a different angle in relation to build layer 116, such that x-ray radiation 109 is received and detected from multiple angles 142 (shown in FIG. 3). In alternative embodiments, imaging device 121 includes a plurality of digital x-ray panels that are positionable, by controller 120, within additive manufacturing system 100. That is, in such embodiments, digital x-ray panels are not stationary, but rather can be positioned around additive manufacturing system 100 to image component 102.

In operation, electron beam 107 is scanned over a portion of build layer 116 forming the most recent build layer 116 that is part of component 106. However, variation in electron beam 107 position and power may form undesirable subsurface features within build layer 116. For example, undesirable subsurface features may include, but are not limited to, a void defined within build layer 116/or between build layers 116, a crack defined within build layer 116 or between build layers 116, or porosity within build layer 116.

As electron beam 107 forms at least a portion of build layer 116, x-ray radiation 109 is generated by interactions between electron beam 107 and material 104. X-rays radiation 109 is directed through pinhole 136 and is detected by imaging device 121. X-rays radiation 109 generated by material 104 around the undesirable subsurface feature will be directed at different angles 142, and as such, imaging device 121 facilitates detecting the undesirable feature. X-ray radiation 109 detected at different angles 142 can then be used to reverse trace the path of x-ray radiation 109 through triangulation, for example, by controller 120, to create a model of build layer 116 or the undesirable feature. Accordingly, the type, size, and depth of the undesirable feature may be identified and determined. If the undesirable feature is detected by imaging device 121, electron beam 107 may be scanned over the undesirable feature when the next build layer(s) 116 is sintered to modify or correct the undesirable feature.

Additionally, a plurality of digital x-ray panels facilitate capturing x-ray radiation 109 at different angles 142. For example, multiple digital x-ray panels can capture x-ray radiation 109 generated around the undesirable feature from multiple angles 142 to create multiple images. These images can then be used to reverse trace the path of x-ray radiation 109 through triangulation, for example, by controller 120, to create a model of build layer 116 or the undesirable feature. Additionally, through use of multiple digital x-ray panels the type, size, and depth of the undesirable feature may be identified and determined.

By imaging x-ray radiation 109 produced by component 102 during the manufacturing process, the time and energy required to detect the undesirable feature is reduced. Specifically, the undesirable features may be detected in-situ, or during the manufacturing process, such that the manufacture of component 102 may be suspended or ceased if the undesirable feature develops during the manufacturing process. The ability to detect and correct undesirable features during the manufacturing process reduces the overall time and cost of production by allowing the manufacturer to correct or stop production of defective components 102 before completion of component 102.

As shown in FIG. 3, pinhole 136 is positioned a first predetermined distance 144 above powder bed 111 and imaging device 121 is positioned a second predetermined distance 146 above pinhole 136. In the exemplary embodiment, first and second predetermined distances 144 and 146 are selected such that imaging device 121 is configured to image the entire powder bed 111 according to geometric optics principles. In the exemplary embodiment, a ratio of first predetermined distance 144 to second predetermined distance 146 is about 0.2 to about 2.0. A pinhole diameter is about 0.05 mm to about 0.5 mm. Additionally, the image generated by imaging device 121 is flipped and inverted.

Figure 4:
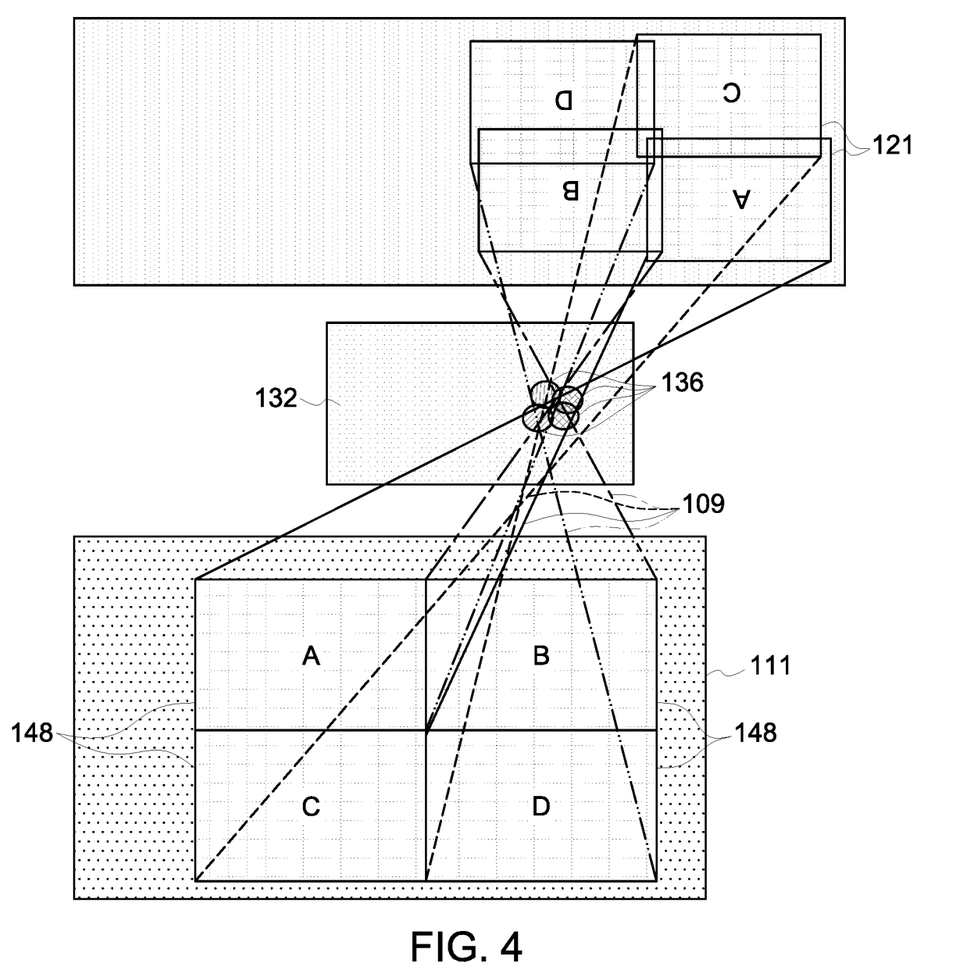
FIG. 4 is a block diagram of an alternative embodiment of the arrangement of an imaging device, a component, and a pinhole relative to each other in the additive manufacturing system shown in FIG. 1.

FIG. 4 is a block diagram of the arrangement of imaging device 121, powder bed 111, and pinholes 136 relative to each other in additive manufacturing system 100 showing composite mosaic imaging with a plurality of digital x-ray panels. In the illustrated embodiment, imaging device 121 includes a plurality of digital x-ray panels and a plurality of pinholes 136 are defined through top side 132. Pinholes 136 are arranged in a tightly spaced arrangement, or a relatively small distance from each other, such that plurality of digital x-ray panels are each configured to image different regions 148 of powder bed 111 simultaneously. In the exemplary embodiment, a distance between pinholes 136 is about 1 mm to about 40 mm. The different images created by plurality of digital x-ray panels are compiled into a single composite mosaic image of powder bed 111. As such, the tightly spaced arrangement along with a plurality of digital x-ray panels allows imaging device 121 to image the entire powder bed 111. Additionally, imaging device 121 facilitates imaging localized predetermined regions 148 of component 102 to inspect for any undesirable subsurface features. This embodiment allows the use of a single pinhole or small number of pinholes to image the whole field of view of the build with a single imaging device.

Figure 5:
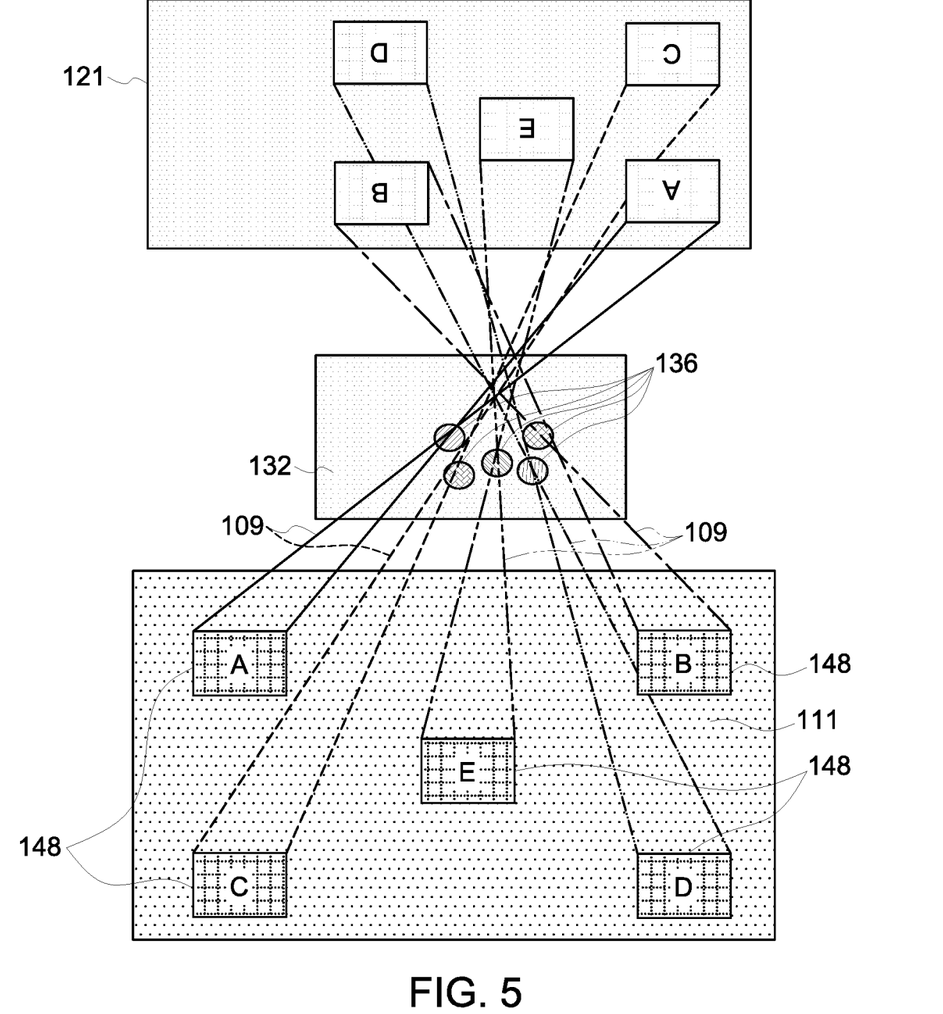
FIG. 5 is a block diagram of an alternative embodiment of the arrangement of an imaging device, a component, and a pinhole relative to each other in the additive manufacturing system shown in FIG. 1.

FIG. 5 is a block diagram of the arrangement of imaging device 121, powder bed 111, and pinholes 136 relative to each other in additive manufacturing system 100 showing multi-area imaging with a single digital x-ray panel. In the illustrated embodiment, imaging device 121 includes a single digital x-ray panel and a plurality of pinholes 136 are defined through top side 132. Pinholes 136 are arranged in an intermediately spaced arrangement, or a medium distance from each other, such that imaging device 121 is configured to image different regions 148 of powder bed 111 simultaneously. This intermediately spaced arrangement along with a single digital x-ray panel allows imaging device 121 to align multiple regions 148 with a single digital x-ray panel. As such, imaging device 121 facilitates imaging localized predetermined regions 148 of component 102 to inspect for any undesirable subsurface features. In some embodiments, imaging device 121 generates multiple images of component 102 and combines the images for a complete representation of component 102. Magnification of the pinhole imaging system (M) is defined as M=L2/L1, where L2 is the distance from pinhole to an image plane (146 in FIG. 3) and L1 is the distance from pinhole to the build plane (144 in FIG. 3). Increase of magnification increases resolution of the system, but decreases the field of view. The use of multiple pinholes allows to access multiple regions of interests with high resolution. A number of pinholes are covering corresponding number of region of interests within a single imaging device. This embodiment allows the use of the smaller format imager while maintaining performance similar to the 2-5× larger imaging device (the cost of the imaging device significantly increases with a sensor size).

Figure 6:
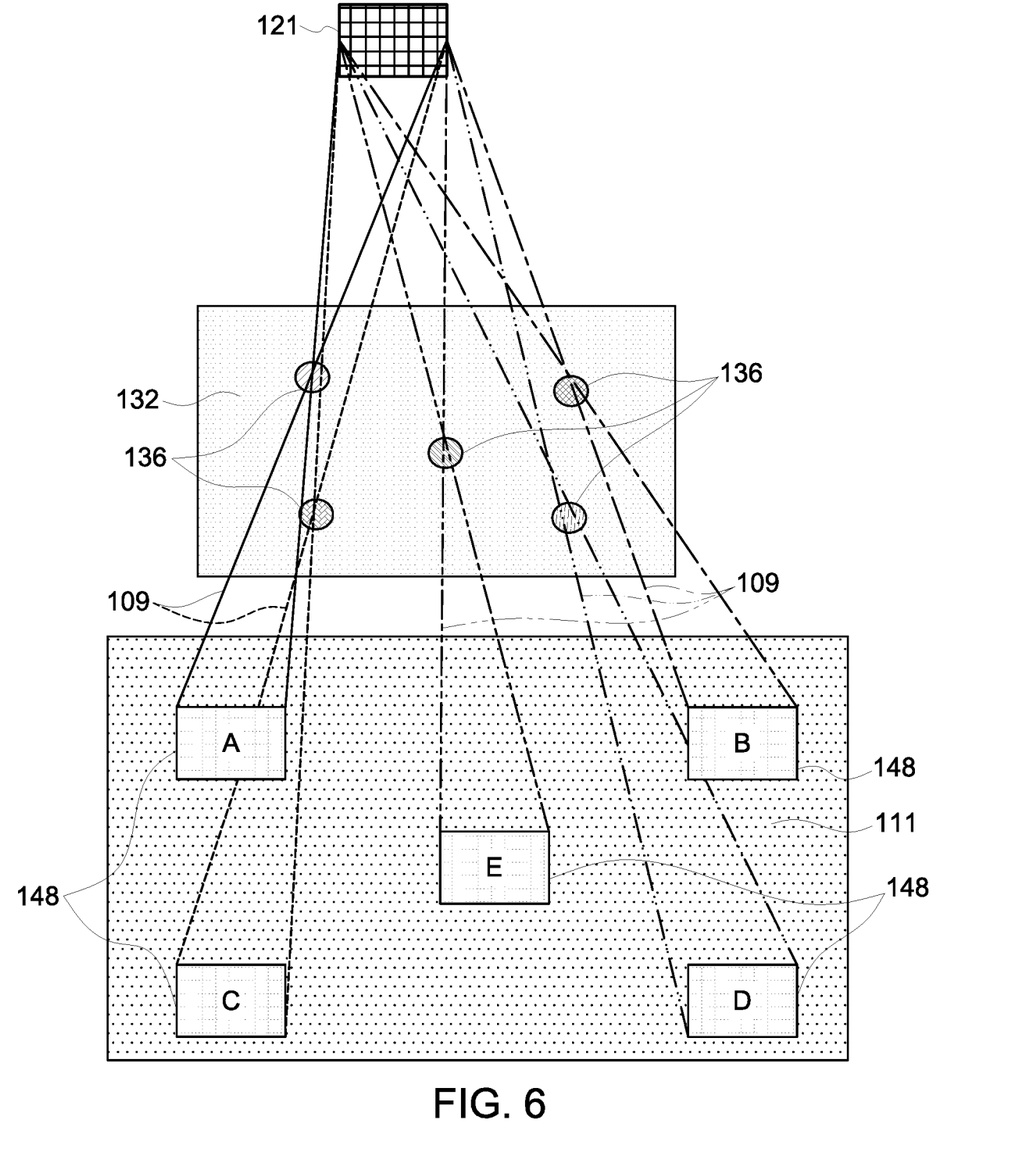
FIG. 6 is a block diagram of an alternative embodiment of the arrangement of an imaging device, a component, and a pinhole relative to each other in the additive manufacturing system shown in FIG. 1.

FIG. 6 is a block diagram of the arrangement of imaging device 121, powder bed 111, and multiple pinholes 136 relative to each other in additive manufacturing system 100 showing multi-spot alignment with a single digital x-ray panel. In the illustrated embodiment, imaging device 121 includes a single digital x-ray panel and a plurality of pinholes 136 are defined through top side 132. Pinholes 136 are arranged in a loosely spaced arrangement, or relatively far from each other, such that imaging device 121 is configured to image different regions 148 of powder bed 111 simultaneously. This loosely spaced arrangement along with a single digital x-ray panel allows imaging device 121 to align multiple regions 148 with a single digital x-ray panel. As such, imaging device 121 facilitates imaging localized predetermined regions 148 of component 102 to inspect for any undesirable subsurface features. In some embodiments, imaging device 121 generates multiple images of component 102 and combines the images for a complete representation of component 102. A high resolution or low cost imager with limited field of view of the region of interest of the build plate (fraction of the total). The build process comprises as sequential rastering of the electron beam in a build plane within a layer. A number of pinholes are covering corresponding number of region of interests with a single imaging device. This particular embodiment is particularly suited for an electron beam calibration method.

Figure 7:
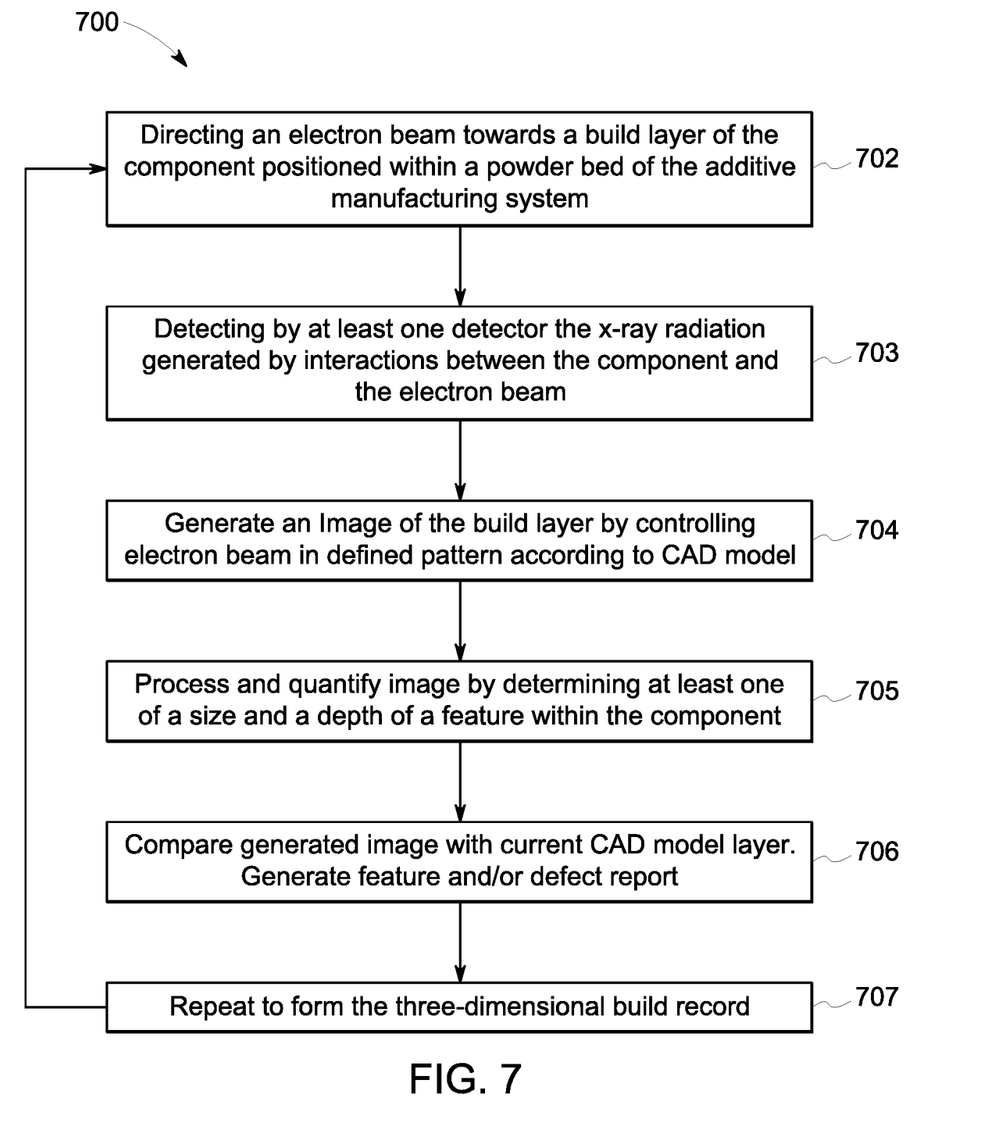
FIG. 7 is a flow diagram of a method of monitoring a component manufactured in the additive manufacturing system shown in FIG. 1.

FIG. 7 is a flow diagram of a method 700 of monitoring component 102 manufactured in additive manufacturing system 100. Method 700 includes directing 702 electron beam 107 towards build layer 116 of component 102 positioned within powder bed 111 of additive manufacturing system 100. Method 700 also includes detecting 703, by at least one detector 121, x-ray radiation 109 generated by interactions between component 102 and electron beam 107. Method 700 also includes automated scanning of the electron beam 108 in defined pattern according to a CAD model and forming image of the layer 704 by at least one detector 121. Method 700 also includes image processing 705 to quantify image by determining at least one of a size and a depth of a feature within component 102. Method 700 also includes real time comparison 706 of detected features with the CAD model and report of the features and defects. The latter could be used for process adjustment feedback or in-process repair. Method 700 further repetition of steps 702 through 706 to form the three-dimensional build record, a feature within component 102.

Figure 8:
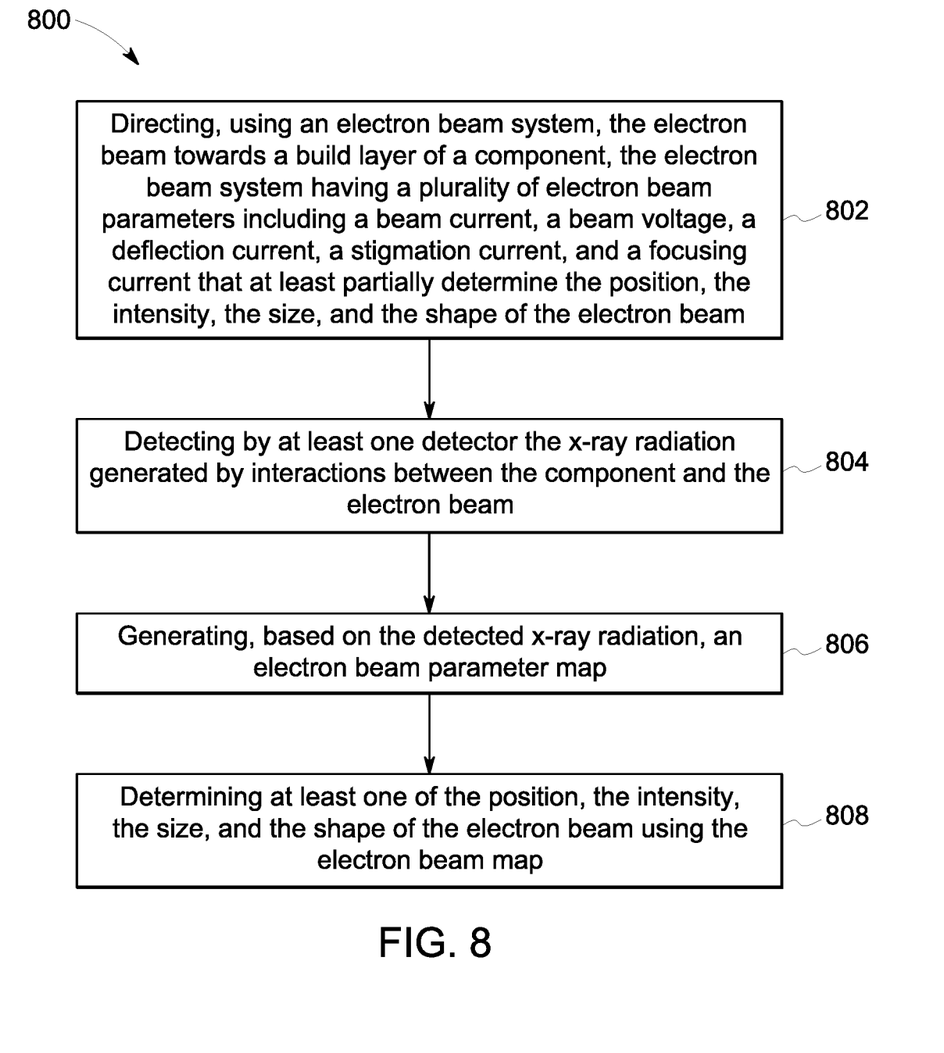
FIG. 8 is a flow diagram of a method of electron beam calibration in the additive manufacturing system shown in FIG. 1.

In addition to the methods described above, additive manufacturing system 100 also calibrates at least a position of electron beam 107 in-situ, or during the manufacturing process. To calibrate the position of electron beam 107, electron beam system 106 directs electron beam 107 toward powder bed 111 with a predetermined beam current and beam voltage. Additionally, scanner system 108 directs electron beam 107 to a predetermined spot on powder bed 111 by passing a predetermined deflection current through the deflection coils. Scanner system 108 also projects electron beam 107 on powder bed 111 with a predetermined size and shape by passing a predetermined stigmation current through the stigmation coils and a predetermined focus current through the focusing coils. Imaging device 121 detects x-ray radiation 109 and detects a position, a size, and/or a shape of electron beam 107 on powder bed 111. Controller 120 records beam current, beam voltage, deflection current, stigmation current, and focus current and the resulting beam energy, electron beam 107 position, the size of electron beam 107, and the shape of electron beam 107, creating an electron beam parameter map. Additive manufacturing system 100 then varies at least one of beam current, beam voltage, deflection current, stigmation current, and focus current which changes at least one of beam energy, electron beam 107 position, the size of electron beam 107, and the shape of electron beam 107. Imaging device 121 detects x-ray radiation 109 and detects a second position, a second size, and/or a second shape of electron beam 107 on powder bed 111. Controller 120 records beam current, beam voltage, deflection current, stigmation current, and focus current corresponding to the resulting second beam energy, second position, the second size, and the second shape of electron beam 107, adding to the electron beam parameter map. Controller 120 creates the electron beam map by recording electron beam parameters while manufacturing component 102. Controller 120 compares the electron beam parameter map to the CAD model of component 102, determining the position of electron beam 107 relative to features of component 102. Controller 120 iterates the calibration process such that the position of electron beam 107 relative to features is continually updated throughout the manufacturing process.

FIG. 8 is a flow diagram of a method 800 of in-situ calibration of the position, intensity, size, and/or shape of electron beam 107 on powder bed 111. Method 800 includes directing 802 the electron beam towards a build layer of a component. The electron beam having a plurality of electron beam parameters including a beam current, a beam voltage, a deflection current, a stigmation current, and a focusing current that at least partially determine the position, the intensity, the size, and the shape of the electron beam. Method 800 also includes detecting 804 by at least one detector the x-ray radiation generated by interactions between the component and the electron beam. Method 800 further includes generating 806, based on the detected x-ray radiation, an electron beam parameter map. Method 800 also includes determining 808 at least one of the position, the intensity, the size, and the shape of the electron beam using the electron beam map. Additionally, the steps of directing 802, detecting 804, generating 806, and determining 808 are repeated at least once, or, in the exemplary embodiment, continuously to determining at least one of the position, the intensity, the size, and the shape of the electron beam.

The above-described imaging devices for additive manufacturing systems overcome a number of deficiencies of known imaging systems and provide a cost-effective method for identifying undesirable features during the additive manufacturing process. Specifically, the embodiments described herein replace known imaging systems that image only a surface of a component build layer. This leads to undesirable subsurface features not being detected until after the additive manufacturing process is completed. More specifically, one exemplary imaging device described herein includes an imaging device that images the component build layer through use of x-rays. High energy electrons strongly interact with the material during the process and produce x-ray radiation which originated in the volume of the material. The x-rays are imaged with an imaging device, allowing the imaging device to image undesirable subsurface features. Through use of x-rays, undesirable subsurface features such as voids, cracks, and porosity are identified. By identifying these subsurface features early in the additive manufacturing process, the manufacturing process can be changed to fix the features and allow for early detection of an unusable component, thereby increasing manufacturing efficiencies.

Additionally, the above described imaging devices for use with additive manufacturing component overcome a number of deficiencies of known imaging systems and provide a cost-effective method for identifying undesirable features during the additive manufacturing process. Specifically, the embodiments described herein replace known 'ex situ' imaging systems such as computer tomography scan systems and digital x-ray systems that are limited as to the size of the manufactured component that may fit within the scanning system. Additionally, the embodiments described herein replace ultrasound imaging systems that require the component surface to be finished. These systems lead to undesirable subsurface features not being detected for large components or until after the component is finished. More specifically, the exemplary imaging devices include an x-ray device that images a localized predetermined area of the component through use of x-rays. In some embodiments, these images are combined to form a complete representation of the component. Through use of the imaging devices, undesirable subsurface features such as voids, cracks, and porosity are identified for large additive manufactured components. As such, external high energy x-ray sources that penetrate through the entire component are not needed. Additionally, the size of the component does not determine what imaging technique to use, as the imaging device size is not a factor. Moreover, the surface of component does not need to be finished before imaging thereby decreasing manufacturing costs for undesirable components.

An exemplary technical effect of the methods and systems described herein includes: (a) imaging undesirable subsurface features using an imaging device; (b) identifying a location, size, and depth of the features for correction; (c) increasing efficiency of the additive manufacturing process through early detection of undesirable features; (d) increasing quality of additive manufacturing components; (e) identifying a location of the features for correction; and (f) quantifying electron beam spot size and coordinates for beam calibration purposes.

Exemplary embodiments of systems and methods for imaging systems for additive manufacturing systems are described above in detail. The methods and systems are not limited to the specific embodiments described herein, but rather, components of systems and steps of the methods may be utilized independently and separately from other components and steps described herein. For example, the method may also be used in combination with other imaging systems, and are not limited to practice only with the additive manufacturing systems as described herein. Rather, the exemplary embodiments can be implemented and utilized in connection with many other applications.

Although specific features of various embodiments of the present disclosure may be shown in some drawings and not in others, this is for convenience only. In accordance with the principles of embodiments of the present disclosure, any feature of a drawing may be referenced and claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, or any other circuit or processing device capable of executing the functions described herein. The methods described herein may be encoded as executable instructions embodied in a computer readable medium, including, without limitation, a storage device or a memory device. Such instructions, when executed by a processing device, cause the processing device to perform at least a portion of the methods described herein. The above examples are exemplary only, and thus are not intended to limit in any way the definition and meaning of the term processor and processing device.

This written description uses examples to disclose the embodiments of the present disclosure, including the best mode, and also to enable any person skilled in the art to practice embodiments of the present disclosure, including making and using any devices or systems and performing any incorporated methods. The patentable scope of the embodiments described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. An additive manufacturing system comprising:
a cabinet configured to enclose a component, said cabinet including a pinhole extending therethrough;
an electron beam system configured to generate an electron beam directed toward the component, wherein interactions between the component and the electron beam generate x-ray radiation;

at least one imaging device configured to detect the x-ray radiation through the pinhole; and a computing device configured to image the component based on the x-ray radiation detected by said at least one imaging device, wherein said at least one imaging device is configured to detect at least one of an air pocket defined within the component, a void defined within the component, and a crack defined within the component.

2. The additive manufacturing system in accordance with claim 1, wherein said at least one imaging device is positioned a first distance above the pinhole.

3. The additive manufacturing system in accordance with claim 2, wherein the pinhole is positioned a second distance above the component.

4. An additive manufacturing system comprising:

a cabinet configured to enclose a component, said cabinet comprising a top side having a top surface, said top side defining at least one pinhole extending therethrough and an electron beam port extending therethrough;

an electron beam system configured to generate an electron beam directed through the electron beam hole toward the component, said electron beam system positioned above said top surface and outside said cabinet, wherein interactions between the component and the electron beam generate x-ray radiation; and at least one imaging device configured to detect the x-ray radiation, said at least one imaging device positioned above said top surface and outside said cabinet, wherein the x-ray radiation is directed through the at least one pinhole toward said at least one imaging device, wherein said at least one imaging device is configured to detect at least one of an air pocket defined within the component, a void defined within the component, and a crack defined within the component.

5. The additive manufacturing system in accordance with claim 4, wherein said at least one imaging device comprises a single imaging device.

6. The additive manufacturing system in accordance with claim 5, wherein the at least one pinhole is a single pinhole.

7. The additive manufacturing system in accordance with claim 5, wherein said at least one imaging device is positioned a first distance above the pinhole.

8. The additive manufacturing system in accordance with claim 7, wherein said single imaging device and the at least one pinhole are configured to image multiple spots on the component.

9. The additive manufacturing system in accordance with claim 5, wherein the at least one pinhole is positioned a second distance above the component.

10. The additive manufacturing system in accordance with claim 9, wherein said single imaging device and the at least one pinhole are configured to image multiple spots on the component.

11. The additive manufacturing system in accordance with claim 4, wherein said at least one imaging device comprises a plurality of imaging devices.

12. The additive manufacturing system in accordance with claim 11, wherein said plurality of imaging devices are positioned a first distance above the pinhole.

13. The additive manufacturing system in accordance with claim 12, wherein said plurality of imaging devices and the at least one pinhole are configured to image multiple regions of the component.

14. A method of monitoring a component manufactured in an additive manufacturing system, said method comprising:

directing an electron beam towards a build layer of the component positioned within a powder bed of the additive manufacturing system;

detecting by at least one detector the x-ray radiation generated by interactions between the component and the electron beam; and determining at least one of a size and a depth of at least one of an air pocket defined within the component, a void defined within the component, and a crack defined within the component.

15. The method in accordance with claim 14 further comprising scanning the electron beam over at least one of the air pocket defined within the component, the void defined within the component, and the crack defined within the component.

16. The method in accordance with claim 14 further comprising modifying at least one of the air pocket defined within the component, the void defined within the component, and the crack defined within the component.

17. The method in accordance with claim 14 further comprising automated scanning of the electron beam on the component in a defined pattern.

18. The method in accordance with claim 14 further comprising comparing, in real time, at least one of the air pocket defined within the component, the void defined within the component, and the crack defined within the component with a CAD model of the component.

19. The method in accordance with claim 14 further comprising repairing at least one of the air pocket defined within the component, the void defined within the component, and the crack defined within the component.

* * * * *